(12) United States Patent
Lang et al.

(10) Patent No.: US 6,503,276 B2
(45) Date of Patent: *Jan. 7, 2003

(54) ACCOMMODATING MULTIFOCAL INTRAOCULAR LENS

(75) Inventors: Alan I. Lang, Long Beach, CA (US); Valdemar Portney, Tustin, CA (US); Stephen W. Laguette, Santa Barbara, CA (US)

(73) Assignee: Advanced Medical Optics, Santa Ana, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/822,040

(22) Filed: Mar. 30, 2001

(65) Prior Publication Data

US 2001/0012964 A1 Aug. 9, 2001

Related U.S. Application Data

(63) Continuation of application No. 09/189,758, filed on Nov. 10, 1998, now Pat. No. 6,231,603.

(51) Int. Cl.$^7$ .................................................. A61F 2/16
(52) U.S. Cl. .................... 623/6.37; 623/6.27; 623/6.28; 623/6.39
(58) Field of Search ................................ 623/6.37, 6.38, 623/6.39, 6.25, 6.27, 6.28; 351/161, 160 R, 159

(56) References Cited

U.S. PATENT DOCUMENTS

| 1,483,509 A | 2/1924 | Bugbee |
| 2,129,305 A | 9/1938 | Feinbloom |
| 2,274,142 A | 2/1942 | Houchin |
| 2,405,989 A | 6/1946 | Beach |

(List continued on next page.)

FOREIGN PATENT DOCUMENTS

| AU | 3225789 | 10/1989 |
| DE | 2702117 | 7/1978 |

(List continued on next page.)

OTHER PUBLICATIONS

Mandell, Contact Lens Practice, 4th Ed.
Holladay et al., J. Cataract Refractive Surg., vol. 14, Jan. 1955.
The Shah Bifocal Intraocular Lens Implant.
Thornton, Color Atlas of Lens Implantation, Accommodation in Pseudophakia, pp. 159–162, 1991.
Video Tape "New Elliptical Acco. IOL For Cataract Surgery" Shown at ASCRS Symposium on Apr. 10, 1999 (Video Enclosed).
Partial Program Re: AGCRS Symposium, Showing Video Tape Shown Between Apr. 10–14, 1999.
Menezo et al J Cataract Refract Surg Aug. 24, 1998.
Fechner et al J Cataract Refract Surg Jan 24, 1998.
World Optics Inc. Opthamology Times, Mar. 15, 1995.
Lolab Corp. Ophthalmology Times, Mar. 15, 1995.
Universe IOL Center, Ocular Surgery News Int'l, no date given.

(List continued on next page.)

*Primary Examiner*—Dinh X. Nguyen
(74) *Attorney, Agent, or Firm*—Stout, Uxa, Buyan & Mullins, LLP; Frank J. Uxa; Peter Jay Gluck

(57) ABSTRACT

Intraocular lenses include a lens body sized and adapted for placement in a mammalian eye and having a plurality of different optical powers, and a movement assembly joined to the lens body and adapted to cooperate with the mammalian eye to effect accommodating movement of the lens body in the eye. Such intraocular lenses provide enhanced accommodation relative to the accommodation attainable using a single optical power IOL adapted for accommodating movement.

20 Claims, 3 Drawing Sheets

U.S. PATENT DOCUMENTS

| | | |
|---|---|---|
| 2,511,517 A | 6/1950 | Spiegel |
| 3,031,927 A | 5/1962 | Wesley |
| 3,034,403 A | 5/1962 | Neefe |
| RE25,286 E | 11/1962 | De Carle |
| 3,210,894 A | 10/1965 | Bentley et al. |
| 3,227,507 A | 1/1966 | Feinbloom |
| 3,339,997 A | 9/1967 | Wesley |
| 3,420,006 A | 1/1969 | Barnett |
| 3,431,327 A | 3/1969 | Tsuetaki |
| 3,482,906 A | 12/1969 | Volk |
| 3,542,461 A | 11/1970 | Girard et al. |
| 3,693,301 A | 9/1972 | Lemaltre |
| 3,922,728 A | 12/1975 | Krasnov |
| 3,932,148 A | 1/1976 | Krewalk, Sr. |
| 4,055,378 A | 10/1977 | Feneberg et al. |
| 4,062,629 A | 12/1977 | Winthrop |
| 4,162,122 A | 7/1979 | Cohen |
| 4,195,919 A | 4/1980 | Shelton |
| 4,199,231 A | 4/1980 | Evans |
| 4,210,391 A | 7/1980 | Cohen |
| 4,240,719 A | 12/1980 | Gullino et al. |
| 4,253,199 A | 3/1981 | Banko |
| 4,254,509 A | 3/1981 | Tennant |
| 4,274,717 A | 6/1981 | Davenport |
| 4,307,945 A | 12/1981 | Kitchen et al. |
| 4,315,673 A | 2/1982 | Guilino et al. |
| 4,338,005 A | 7/1982 | Cohen |
| 4,340,283 A | 7/1982 | Cohen |
| 4,370,760 A | 2/1983 | Kelman |
| 4,377,329 A | 3/1983 | Poler |
| 4,402,579 A | 9/1983 | Poler |
| 4,404,694 A | 9/1983 | Kelman |
| 4,409,691 A | 10/1983 | Levy |
| 4,418,991 A | 12/1983 | Breger |
| 4,476,591 A | 10/1984 | Arnott |
| 4,504,982 A | 3/1985 | Burk |
| 4,551,864 A | 11/1985 | Akhavi |
| 4,560,383 A | 12/1985 | Leiske |
| 4,573,775 A | 3/1986 | Bayshore |
| 4,580,882 A | 4/1986 | Nuchman et al. |
| 4,596,578 A | 6/1986 | Kelman |
| 4,618,228 A | 10/1986 | Baron et al. |
| 4,618,229 A | 10/1986 | Jacobstein et al. |
| 4,636,049 A | 1/1987 | Blaker |
| 4,636,211 A | 1/1987 | Neilsen et al. |
| 4,637,697 A | 1/1987 | Freeman |
| 4,641,934 A | 2/1987 | Freeman |
| 4,687,484 A | 8/1987 | Kaplan |
| 4,693,572 A | 9/1987 | Tsnetaki et al. |
| 4,702,244 A | 10/1987 | Mazzocco |
| 4,704,016 A | 11/1987 | De Carle |
| 4,720,286 A | 1/1988 | Bailey et al. |
| 4,725,278 A | 2/1988 | Shearing |
| 4,752,123 A | 6/1988 | Blaker |
| 4,759,762 A | 7/1988 | Grendahl |
| 4,769,033 A | 9/1988 | Nordan |
| 4,790,847 A | 12/1988 | Woods |
| 4,813,955 A | 3/1989 | Achatz et al. |
| 4,830,481 A | 5/1989 | Futhey et al. |
| 4,842,601 A | 6/1989 | Smith |
| 4,881,804 A | 11/1989 | Cohen |
| 4,888,012 A | 12/1989 | Hom et al. |
| 4,888,015 A | 12/1989 | Domino |
| 4,890,912 A | 1/1990 | Visser |
| 4,890,913 A | 1/1990 | De Carle |
| 4,892,543 A | 1/1990 | Turley |
| 4,898,461 A | 2/1990 | Portney |
| 4,906,246 A | 3/1990 | Grendahl |
| 4,917,681 A | 4/1990 | Nordan |
| 4,919,663 A | 4/1990 | Grendahl |
| 4,921,496 A | 5/1990 | Grendahl |
| 4,923,296 A | 5/1990 | Erickson |
| 4,932,966 A | 6/1990 | Christie et al. |
| 4,932,968 A | 6/1990 | Caldwell et al. |
| 4,938,583 A | 7/1990 | Miller |
| 4,976,534 A | 12/1990 | Miege et al. |
| 4,976,732 A | 12/1990 | Vorosmarthy |
| 4,990,159 A | 2/1991 | Kraff |
| 4,994,082 A | 2/1991 | Richards et al. |
| 5,000,559 A | 3/1991 | Takahashi et al. |
| 5,002,382 A | 3/1991 | Seidner |
| 5,019,098 A | 5/1991 | Mercier |
| 5,019,099 A | 5/1991 | Nordan |
| 5,047,052 A | 9/1991 | Dubroff |
| 5,089,024 A | 2/1992 | Christie et al. |
| 5,096,285 A | 3/1992 | Silberman |
| 5,112,351 A | 5/1992 | Christie et al. |
| 5,147,397 A | 9/1992 | Christ et al. |
| 5,166,711 A | 11/1992 | Portney |
| 5,166,712 A | 11/1992 | Portney |
| 5,171,266 A | 12/1992 | Wiley et al. |
| 5,173,723 A | 12/1992 | Volk |
| 5,192,317 A | 3/1993 | Kalb |
| 5,192,318 A | 3/1993 | Schneider |
| 5,225,858 A | 7/1993 | Portney |
| 5,260,727 A | 11/1993 | Oksman et al. |
| 5,270,744 A | 12/1993 | Portney |
| 5,275,623 A | 1/1994 | Sartarazi |
| 5,354,335 A | 10/1994 | Lipshitz et al. |
| 5,443,506 A | 8/1995 | Garabet |
| 5,476,514 A | 12/1995 | Cumming |
| 5,489,302 A | 2/1996 | Skottun |
| 5,496,366 A | 3/1996 | Cumming |
| 5,521,656 A | 5/1996 | Portney |
| 5,549,760 A | 8/1996 | Becker |
| 5,562,731 A | 10/1996 | Cumming |
| 5,578,081 A | 11/1996 | McDonald |
| 5,607,472 A | 3/1997 | Thompson |
| 5,628,795 A | 5/1997 | Langerman |
| 5,628,796 A | 5/1997 | Suzuki |
| 5,652,638 A | 7/1997 | Roffman et al. |
| 5,657,108 A | 8/1997 | Portney |
| 5,674,282 A | 10/1997 | Cumming |
| 5,682,223 A | 10/1997 | Menezes et al. |
| 5,684,560 A | 11/1997 | Roffman et al. |
| 5,766,244 A | 6/1998 | Binder |
| 5,769,890 A | 6/1998 | McDonald |
| 5,814,103 A | 9/1998 | Lipshitz et al. |
| 5,843,188 A | 12/1998 | McDonald |
| 5,876,442 A | 3/1999 | Lipshitz et al. |
| 6,096,078 A | 8/2000 | McDonald |
| 6,013,101 A1 | 1/2001 | Israel |
| 6,176,878 B1 | 1/2001 | Gwon et al. |
| 6,217,612 B1 | 4/2001 | Woods |

FOREIGN PATENT DOCUMENTS

| | | |
|---|---|---|
| DE | 3246306 | 6/1984 |
| EP | 939016 | 10/1963 |
| EP | 0246216 | 11/1987 |
| EP | 0329981 | 8/1989 |
| EP | 337390 | 10/1989 |
| EP | 0342895 | 11/1989 |
| EP | 0351471 | 1/1990 |
| EP | 0566170 | 10/1993 |
| EP | 0691109 | 1/1996 |
| EP | 0897702 | 2/1999 |
| GB | 2124500 | 2/1984 |
| GB | 2129155 | 5/1984 |
| GB | 2146791 | 4/1985 |
| GB | 2192291 | 1/1988 |
| GB | 2215076 | 9/1989 |

| | | |
|---|---|---|
| IL | 2058391 | 4/1981 |
| WO | 8603961 | 7/1986 |
| WO | 8700299 | 1/1987 |
| WO | 8707496 | 12/1987 |
| WO | 8902251 | 3/1989 |
| WO | 8911672 | 11/1989 |
| WO | 9416648 | 8/1994 |
| WO | 9503783 | 2/1995 |
| WO | 9615734 | 5/1996 |
| WO | 9625126 | 8/1996 |
| WO | 9743984 | 11/1997 |
| WO | 0134061 | 5/2001 |
| ZA | 888414 | 11/1988 |

OTHER PUBLICATIONS

Hanita Lenses, Ocular Surgery, News Int'l, no date given.
Alcon Surgical, Aleon Laboratories, no date given.
Mediphacos Ltda. Ocular Surgery News, Int'l, no date given.
Storz Ophthalmics Inc. Model Lizzuv ACL. no date given.
Opthamed Inc. OMAC–260, no date given.
Chaurin–Opsia, Azurite ACL(0459) no date given.
Amo Specs Model AC–218, 1992.
Chiron, Clemente Optifit Modell SPSP625 Brochure Translation, Dec. 1998.
Chiron Vision.Nurita Ma20,1997.

ACCOMMODATING MULTIFOCAL INTRAOCULAR LENS

This is a continuation of application Ser. No. 09/189,758, now U.S. Pat. No. 6,231,603, filed Nov. 10, 1998, the disclosure of which is hereby incorporated in its entirety herein by reference.

BACKGROUND OF THE INVENTION

The present invention is directed to intraocular lenses (IOLs). More particularly, the invention relates to IOLs which have a plurality of optical powers and, in addition, are adapted to provide accommodating movement in the eye.

The human eye includes an anterior chamber between the cornea and iris, a posterior chamber, defined by a capsular bag, containing a crystalline lens, a vitreous chamber behind the lens containing the vitreous humor, and a retina at the rear of this chamber. The human eye has a natural accommodation ability. The constriction or contraction and relaxation of the ciliary muscle provides the eye with near and distant vision, respectively. This ciliary muscle action shapes the natural crystalline lens to the appropriate optical configuration for focussing light rays entering the eye on the retina.

After the natural crystalline lens is removed, for example, because of cataract or other condition, a conventional, monofocal IOL can be placed in the posterior chamber. Such a conventional IOL has very limited, if any, accommodating ability. However, the wearer of such an IOL continues to require the ability to view both near and far (distant) objects. Corrective spectacles may be employed as a useful solution. Recently multi-focal IOLs without accommodating movement have been used to provide vision correction.

Attempts have been made to provide IOLs with accommodating movement along the optical axis of the eye as an alternative to shape changing. Examples of such attempts are set forth in Levy U.S. Pat. No. 4,409,691 and several patents to Cumming, including U.S. Pat. Nos. 5,674,282 and 5,496,366. The disclosure of each of these patents is incorporated herein by reference. One problem that exists with IOLs which are adapted for accommodating movement toward and away from the retina of the eye is that such IOLs often cannot move sufficiently to obtain the desired accommodation because of space constraints within the eye. The present inventors are unaware of any so-called accommodating IOL which provides the desired degree of accommodation.

It would be advantageous to provide IOLs adapted for accommodating movement which can achieve an increased amount of accommodation with readily attainable amounts of accommodating movement.

SUMMARY OF THE INVENTION

New accommodating IOLs have been discovered. The present IOLs provide enhanced accommodation with a relatively limited, and readily attainable amount of accommodating movement. The present accommodating IOLs take advantage of one or more components and/or other features of the eye to provide for the accommodating movement. For example, accommodating movement can be provided by action of the ciliary muscle of the eye and/or of the zonules of the eye and/or by the vitreous pressure within the eye. Further, the optic or lens body of the IOL has a plurality of different optical powers, that is it is multifocal. Such lens body can be refractive or diffractive.

The combination of an IOL which is adapted to cooperate with the eye to provide accommodating movement and a multifocal lens body provides substantial advantages. For example, the multifocal lens body allows substantially enhanced effective or apparent accommodation with a readily attainable amount of accommodating movement in the eye. By providing an IOL having a near vision correction power, as well as an intermediate and/or baseline and/or far vision correction power, enhanced apparent accommodation, for example, on the order of about 3.5 diopters of accommodation, particularly for viewing near objects, is readily obtained with relatively limited amounts of accommodating movement of the IOL. In addition, the accommodating movement of the present IOLs preferably provides for enhanced intermediate vision and an advantageously greater range of near vision as compared with current multifocal IOLs which are not adapted for substantial accommodating movement. The present IOLs are straightforward in construction, employ conventional or standard IOL materials of construction, are easy to produce and implant in the eye and provide outstanding results.

In one broad aspect of the invention, IOLs are provided which comprise a lens body sized and adapted for placement in a mammalian, for example, human, eye. This lens body has a plurality of different optical powers, that is the lens body is multifocal. The IOLs further include a movement assembly which is joined to the lens body of the IOL. The movement assembly is adapted to cooperate with the mammalian eye to effect accommodating movement of the lens body in the eye. Thus, the wearers of the present IOLs are provided with accommodation benefits obtained from the multifocal lens body and accommodating movement of the lens body.

In one useful embodiment, the lens body has a first optical power for near vision and a second optical power for far vision. Optionally, the transition between the near vision optical power and the far vision optical power may be progressive. The lens body may have a third optical power intermediate between the first and second optical powers.

The lens body preferably includes a plurality of different regions each having a different optical power. In one very useful embodiment, the lens body includes a plurality of annular zones extending radially outwardly from the central or optical axis of the lens body. The lens body of the present IOLs can have the optical characteristics of the optics of Portney U.S. Pat. Nos. 4,898,461 and 5,225,858, the disclosure of each of which is incorporated by reference herein.

The movement assembly preferably is adapted to cooperate with the ciliary muscle and/or the zonules of the mammalian eye and/or with the vitreous pressure in the eye to effect accommodating movement of the lens body in the eye. More preferably, the movement assembly is adapted to cooperate with the ciliary muscle and/or zonules of the mammalian eye and/or with the vitreous pressure in the eye to move the lens body toward a first position relative to the retina of the eye, for example, when the ciliary muscle is relaxed, and toward a different second position, for example, when the ciliary muscle is constricted or contracted. The first position of the lens body preferably enhances far vision whereas the second position of the lens body preferably enhances near vision. In one embodiment, the movement assembly comprises at least one biasing member, and preferably a plurality of biasing members, coupled to the lens body. The biasing member can be a spring or similar element. The movement assembly can be as disclosed in Levy U.S. Pat. No. 4,409,691, noted previously.

The movement assembly may comprise at least one fixation member, and preferably a plurality of fixation members, including a proximal end region coupled to the lens body and a distal end region extending away from the lens body and adapted to contact a capsular bag, for example, the posterior capsular bag, of the mammalian eye. In this embodiment, the action of the eye, for example, the ciliary muscle and/or the zonules, preferably acts directly on the fixation member or members which transfer the force to the lens body causing the accommodating movement of the lens body. A representative movement assembly including fixation members is set forth in the above-noted Cumming patents. One or more different approaches can be employed to couple the distal end region of the fixation member to the capsular bag. Examples of such approaches include the use of adhesives, fibrosis of the capsular bag, suturing and the like surgical techniques, and combinations thereof. If fixation member or members are used to transfer the force of the eye to the lens body to effect accommodating movement, preferably the fixation member or members are secured, more preferably fixedly secured, to the eye, and in particular, to the capsular bag of the eye.

In another broad aspect of the present invention, combination lens systems are provided which include an IOL, as discussed above, including a multifocal lens body and a movement assembly; and, in addition, a lens element adapted for implantation in the eye; preferably in a substantially fixed position in the eye, for example, adapted for implantation in the capsular bag of the eye, more preferably in contact with the capsular bag, for example, the posterior capsular bag or the equator of the capsular bag, of the eye.

The lens element preferably is adapted to reduce cell growth in the posterior capsular bag in the space defined by the capsular bag of the eye. Thus, the lens element is effective in reducing secondary opacification which may occur as the result of the implantation of the IOL.

Each of the lens body and the lens element of the above-noted lens combination has an optical axis and a maximum cross sectional area perpendicular to the optical axis. The lens element may have a larger or smaller maximum cross sectional area perpendicular to the optical axis than does the lens body. The relatively large or wide lens element facilitates inhibiting the growth of cells in the space formed by the capsular bag. Such inhibition preferably is sufficient to allow the multifocal lens body to effectively provide the desired vision correction to the wearer of the lens combination without substantial interference from such cell growth. The lens element preferably has a single optical power. Preferably, both the intraocular lens and the lens element of the combination are adapted for implantation in the posterior capsular bag of the mammalian eye with the lens body being located anterior of the lens element. To provide an enhanced degree of stability between the IOL and the lens element, one or more filaments or other structure(s) may be located between the lens body and lens element to facilitate substantial alignment between these two components.

Any feature or combination of features described herein is included within the scope of the present invention provided that the features of any such combination are not mutually inconsistent.

Additional aspects and advantages of the present invention are set forth in the following description and claims, particularly when considered in conjunction with the accompanying drawings in which like parts bear like reference numerals.

DETAILED DESCRIPTION OF THE DRAWINGS

Figure 1:
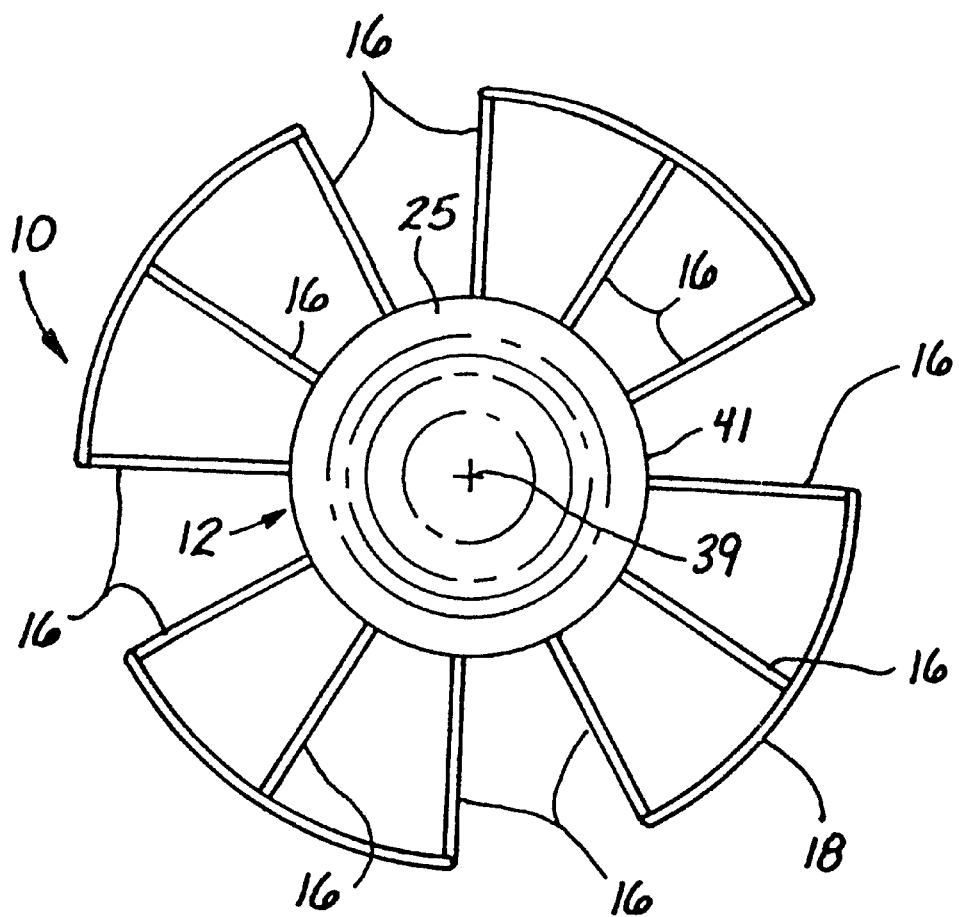
FIG. 1 is a front elevational view of an intraocular lens in accordance with one embodiment of the invention.
Figure 2:
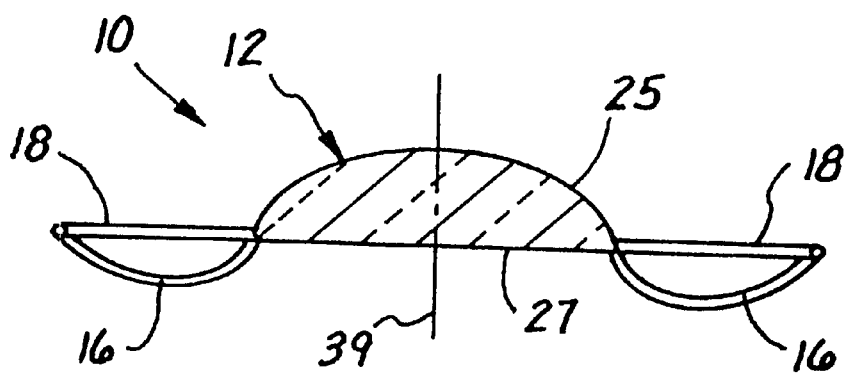
FIG. 2 is a cross sectional view of the intraocular lens shown in FIG. 1.

Referring now to FIGS. 1 and 2, an intraocular lens (IOL) according to the present invention, shown generally at 10, includes a multifocal lens body 12 having a plurality of optical powers, as described hereinafter. Radially extending struts 16 are molded integrally with the lens body 12 and are terminated at their outer ends by arcuate rim portions 18. The struts 16 are long enough so that the rim portions 18 are in light pressure contact with the perimeter of the posterior capsular bag when the lens 10 is implanted in the eye.

The lens body 12 may be constructed of rigid biocompatible materials, such as polymethyl methacrylate (PMMA), or flexible, deformable materials, such as silicone polymeric material, acrylic polymeric material, hydrogel polymeric material and the like, which enable the lens body to be rolled or folded for insertion through a small incision into the eye. Although the lens body 12 as shown is a refractive lens body, the present IOLs can include a diffractive lens body and such embodiment is included within the scope of the present invention.

Figure 3:
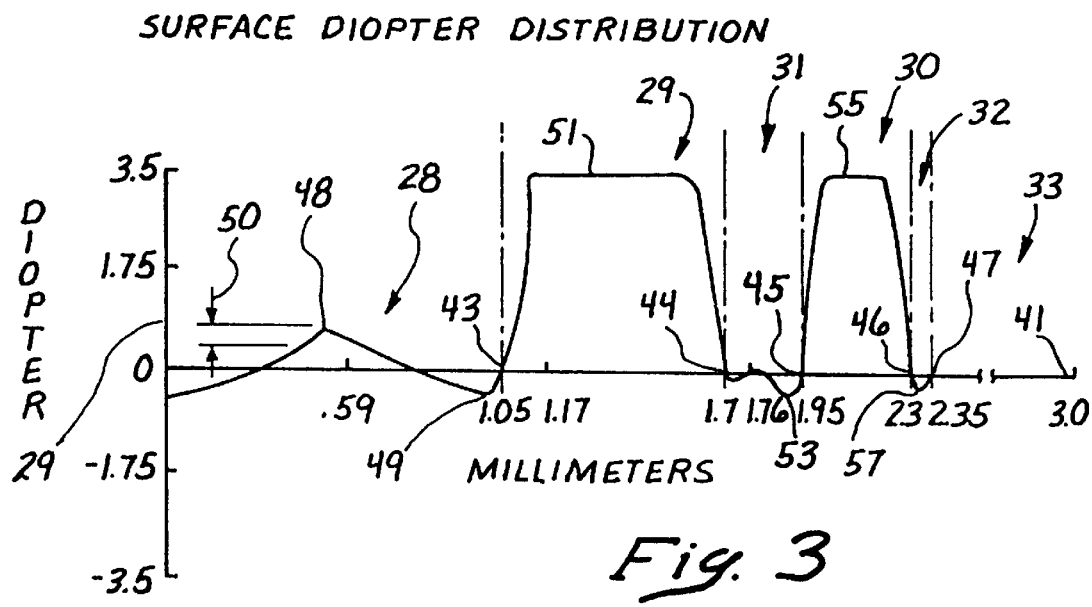
FIG. 3 is a plot of the power of the lens body of the IOL shown in FIG. 1 versus distance from the optical axis of the IOL.

With particular reference to FIG. 3, the lens body 12 has a central zone 28, inner and outer annular near zones 29 and 30 and annular far zones 31, 32 and 33. In this embodiment, the central zone 28 is circular and the peripheries of the annular zones 29–33 are circular. The annular zones 29–33 circumscribe the central zone 28 and the zones are contiguous. The zones 29–33 are concentric and coaxial with the lens body 12.

The zones 28–33 are used in describing the vision correction power of the lens body 12, and they are arbitrarily defined. Thus, the peripheries of the zones and the number of zones may be selected as desired. Although the boundaries of the zones are indicated by phantom lines in FIG. 1, it should be understood that the lens body 12 has no such lines in any of its surfaces and that these lines are provided for illustrative purposes.

In the embodiment of FIGS. 1 and 2, the lens body 12 has a convex anterior surface 25 and a planar posterior surface 27; however, these configurations are merely illustrative. Although the vision correction power may be placed on either of the surfaces 25 or 27, in this embodiment the anterior surface 25 is appropriately shaped to provide the desired vision correction powers.

FIG. 3 shows the preferred manner in which the vision correction power of the lens body 12 varies from the center of optical axis 39 of the optic to the circular outer periphery 41 of the optic. In FIG. 3, the vertical or "Y" axis represents the variation in diopter power of the lens body 12 from the baseline or far vision correction power, and the "X" or horizontal axis shows the distance outwardly from the optical axis 39 in millimeters. Thus, the zero-diopter or baseline power of FIG. 3 is the power required for far vision for an IOL. The power variation shown in FIG. 3 is applicable to any radial plane passing through the optical axis 39. In other words, the power at any given radial distance from the optical axis 39 is the same.

The central zone 28 extends from the optical axis 39 to a circular periphery 43, the inner annular near zone 29 is considered as extending from the periphery 43 to a circular periphery 44, and the outer annular near zone is considered as extending from a periphery 45 to a periphery 46. The annular far zone 31 extends between the peripheries 44 and 45, and the annular far zone 32 extends from the periphery 46 radially outwardly to a periphery 47. The annular zone 33 extends from the periphery 47 radially outwardly to the outer periphery 41 of the lens body 22. As shown in FIG. 3, the vision correction power crosses the "X" axis or baseline at the peripheries 43, 44, 45, 46 and 47.

As shown in FIG. 3, the vision correction power varies from a negative diopter power at the optical axis 39 through a baseline diopter correction power to an apex 48 and then decreases continuously and progressively from the apex 48 back through the baseline diopter correction to another negative diopter power at a point 49. The negative diopter powers at the optical axis and the point 49 are of less power than is required for far vision and may be considered as far, far vision correction powers. From the point 49, the vision correction power increases through the periphery 43 into the inner annular near zone 29. Of course, the diopters shown on the ordinate in FIG. 3 are merely exemplary, and the actual correction provided by the plurality of optical powers will vary and depends, for example, on the amount of accommodating movement obtained and on the needs of the patient.

The apex 48 has a vision correction power for intermediate vision. The intermediate vision correction may be considered as being in a zone 50 which may be between 0.5 and 0.75 diopters from the baseline diopter power. The far vision correction powers may be considered as lying between the zone 50 and the baseline diopter correction, and the far, far vision correction powers are negative. The intermediate, far and far, far powers combine to provide a mean power in the central zone 28 for far vision.

Within the inner annular near zone 29, the vision correction power varies from the periphery 43 to a plateau 51, and from the plateau, the vision correction power varies back to the periphery 44 at the baseline. In the far zone 31, the vision correction power increases very slightly above the baseline and then proceeds to a far, far negative vision correction power at a point 53 at which the vision correction power reverses and returns to the baseline at the periphery 45.

In the outer annular near zone 30, the power varies from the periphery 45 to a plateau 55 and returns from the plateau 55 to the baseline at the periphery 46. In the far zone 32, the power dips slightly below the baseline to a point 57 in the far, far correction region and then returns to the baseline at the outer periphery 47. The dips below the baseline to the points 53 and 57 in the far zones 31 and 32 help support the increased depth of the focus of the central zone 28.

The far zone 33 has a vision power that lies along the baseline and is configured for far vision. The zone 33, which lies radially outwardly of a diameter of about 4.7 mm, is only usable in poor light conditions when the pupil is vary large. Under poor lighting conditions such as this, far vision is all that is normally required.

The inner near zone 29 has regions adjacent the peripheries 43 and 44 with far vision correction powers and a second region, which includes the plateau 51 with near vision correction powers. Similarly, the outer near zone 30 has regions adjacent the peripheries 45 and 46 with far vision correction powers and a second region, which includes the plateau 55, with near vision correction powers. For example, the near vision powers may be those which are above about 2 or 2.5 diopters. The 2 to 2.5 diopters correspond to about 20 to about 16 inches, respectively, of working distance, and this distance corresponds to the beginning of near activities.

As shown in FIG. 3, each of the these "near" regions has a major segment, i.e., the plateaus 51 and 55 in which the near vision correction power is substantially constant. The plateau 51, which lies radially inwardly of the plateau 55, has a greater radial dimension than the plateau 55. The difference in radial dimensions of the plateaus 51 and 55 allows these two plateaus to have approximately the same area.

It can be seen from FIG. 3 that the vision correction power of the central zone is continuously variable and that the vision correction power of the entire optic, except for the plateaus 51 and 55, is continuously variable. The apex 48 is the greatest diopter power of the central zone 28, and the negative diopter power at the optical axis 39 and the points 40, 53 and 57 is blended smoothly with the vision correction powers radially outwardly thereof.

Figure 4:
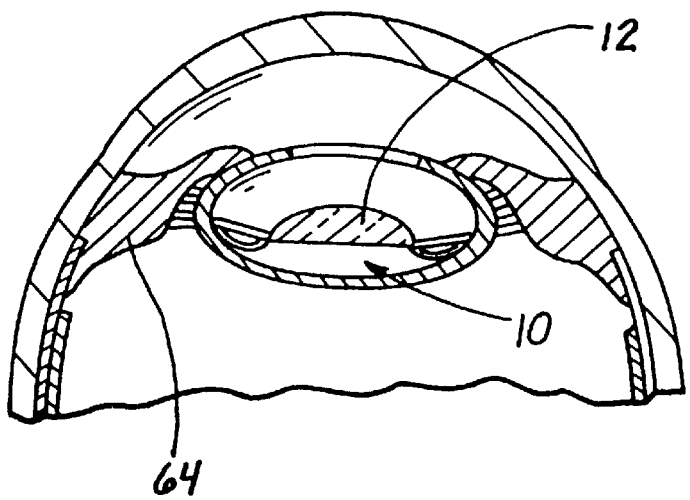
FIG. 4 is a fragmentary sectional view of an eye in which the intraocular lens of FIG. 1 has been implanted.

With reference to FIG. 4, when the ciliary muscle 64 contracts, as it normally does when the eye tries to focus on a nearby object, it drives the outer ends of the struts 16 radially inwardly thus forcing the lens body 12 forwardly, away from the retina. As the ciliary body 64 relaxes the struts 16 act as springs to retract the lens body 12 back to its original position for distance focus.

Because the lens body 12 is multifocal, the combined accommodating effects of the movement of the lens body and its multifocal characteristics provide enhanced accommodation. Enhanced apparent accommodation for near vision, for example, relative to a similarly configured IOL having only a monofocal vision correction adapted for accommodating movement, is achieved. Also, the combined accommodating movement/multifocal characteristics of the present IOL are particularly effective in providing intermediate vision, that is vision between near objects and far objects, and enhance the range of the near vision as compared with a similar multifocal IOL which does not provide for accommodating movement.

Figure 5:
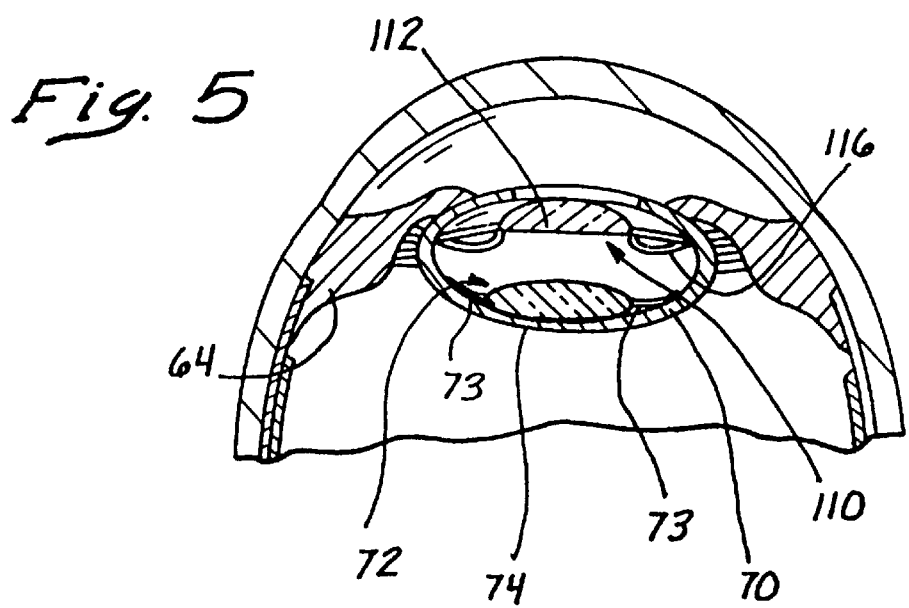
FIG. 5 is a fragmentary sectional view of an eye in which a lens combination according to the present invention has been implanted.

A lens system comprising IOL 110 and posterior lens element 72 is illustrated in FIG. 5. IOL 110 is structured and functions similarly to IOL 10. Components of IOL 110 which correspond to components of IOL 10 are identified with the same reference numeral increased by 100.

Posterior lens element 72 is positioned centrally within the capsule 70 in contact with the posterior wall 74 thereof. It remains in this position, for example because of one or more fixation members. To illustrate, fixation members, in the form of filaments 73 of polypropylene or the like polymeric materials, coupled to the posterior lens element 72 and extending outwardly therefrom come in contact with the capsular wall to at least assist in maintaining lens element 72 in the desired posterior position. The IOL 110 of the combination shown in FIG. 5 is supported by struts 116 that extend rearwardly and radially outwardly to the wall of the capsule 70 into engagement with the perimeter of capsule. The IOL 110 shown in FIG. 5 functions in a manner similar to the IOL 10 shown in FIG. 4, described previously. Thus, lens body 112 can be moved forwardly (as shown in FIG. 4) to provide near vision accommodation or can be retracted back to a position closer to the retina for distance focus. The presence of lens element 72 is effective to inhibit cell growth from the capsule into the space defined by the capsule. This promotes vision clarity and allows for long term maintenance of the combination. In addition, lens element 72, which has a single optical power, may provide effective vision correction in combination with the multifocal lens body 112.

Figure 6:
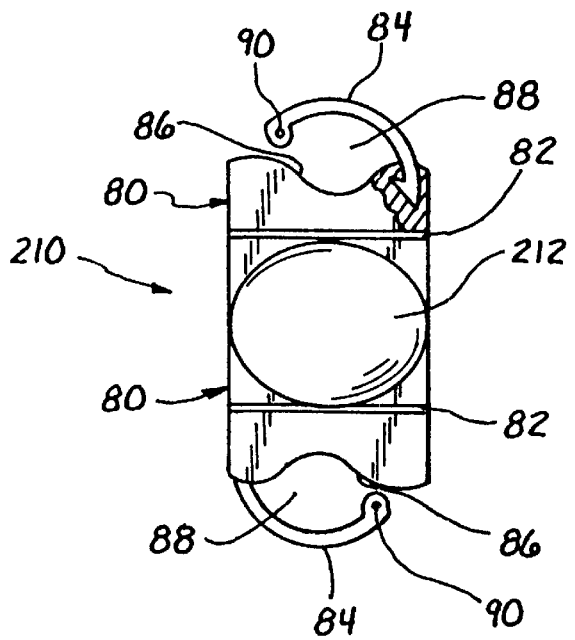
FIG. 6 is a front elevational view of another embodiment of an intraocular lens in accordance with the present invention.

FIG. 6 illustrates another embodiment of a IOL, shown generally at 210, in accordance with the present invention. IOL 210 is structured somewhat similarly to IOL 10. Components of IOL 210 which correspond to components of IOL 110 are identified with the same reference numeral increased by 200.

The primary difference between IOL 210 and IOL 10 is the inclusion of plate haptics 80 in the IOL 210. The lens body 212 of IOL 210 has a similar optical profile as illustrated with regard to lens body 12. Each of the flexible plate haptics 80 has a hinge 82 formed by a groove in the anterior side of IOL 210, and a spring 84 at the end of each of the plate haptics 80. These haptics 80 are joined to, for example, are unitary with, the lens body 210. The springs 84 are resilient loops which are staked at one end to the end of the haptic 80 at opposite sides of the longitudinal center line of the IOL 210. These spring loops 84 bow outwardly lengthwise of the lens body 212 from their staked ends to their center and then turn back toward the lens body from their centers to their free ends. The ends of the haptics 80 have recesses 86 over which the spring loops 84 extend in such a way that the loops and the edges of the recesses form openings 88 therebetween. The ends of the spring loops 84 have holes 90 to receive instruments for positioning the IOL 210 in the eye.

IOL 210 is implanted within the capsular bag within the eye while the ciliary muscle is paralyzed in its relaxed state and the capsular bag is thereby stretched to its maximum diameter. The overall length of the IOL 210 measured between the ends of the haptics 80 at either of the haptic recesses 86 substantially equals the inner diameter of the stretched capsular bag. The overall length of the IOL 10 measured between the outer edges of the loop springs 84 at their centers when the loops are in their normal unstressed condition or state is slightly greater than the inner diameter of the capsular bag.

IOL 210 is particularly used when the interior capsular remnant or rim of the capsular bag is ruptured, that is, cut or torn. When IOL 210 is implanted in the capsular bag, the loop springs 84 press outward against the wall of the capsular bag sulcus to fixate the lens in the bag during fibrosis. Fibrosis occurs in such a way as to effect fusion of the anterior remnant to the posterior capsule. Constriction and relaxation of the ciliary muscle after fibrosis facilitates accommodating movement of the IOL 210. The IOL 210 utilizes the fibrosed interior capsular rim, the elastic posterior capsule, the vitreous cavity pressure, the zonules and the ciliary muscle constrictions, together with the multifocal lens body 212, to provide accommodating movement forward, for example, for near vision. Relaxation of the ciliary muscle stretches the capsular bag and the fibrosed anterior capsular rim to return the lens rearwardly toward its distant vision position.

The present IOLs very effectively provide for enhanced accommodation in cooperation with the eye. Thus, the accommodating movement of the IOL, together with the multifocal characteristics of the lens body of the present IOL, provide substantially enhanced performance, for example, relative to a monofocal IOL adapted for accommodating movement or a multifocal IOL located in a substantially fixed position within the eye. Further, it should be understood that the present IOLs can be provided with multifocal characteristics using any suitable methodology. Also, the IOL can be configured to provide any suitable multifocal arrangement of optical powers. In addition, the present IOLs can be constructed to obtain accommodating movement in any suitable manner. The exemplary embodiments illustrated herein are presented for illustrative purposes and are not intended to be limiting to the broad scope of the present invention.

While this invention has been described with respect to various specific examples and embodiments, it is to be understood that the invention is not limited thereto and that it can be variously practiced within the scope of the following claims.

What is claimed is:

1. An intraocular lens comprising:
   a lens body sized and adapted for placement in a mammalian eye and having a central axis and a plurality of different optical powers, the lens body including a central region about the central axis and at least one annular region extending radially outwardly from the central axis, the central region and the at least one annular region each having a different optical power; and
   a movement assembly joined to the lens body and adapted to cooperate with the mammalian eye to effect accommodating movement of the lens body in the eye.

2. The intraocular lens of claim 1 wherein the lens body has a first optical power for near vision and a second optical power for far vision.

3. The intraocular lens of claim 2 wherein the lens body has a third optical power intermediate between the first and second optical powers.

4. The intraocular lens of claim 1 wherein the movement assembly comprises at least one biasing member coupled to the lens body.

5. The intraocular lens of claim 4 wherein the biasing member comprises a spring member.

6. The intraocular lens of claim 1 wherein the lens body includes a plurality of annular regions extending radially outwardly from the central axis of the lens body.

7. The intraocular lens of claim 6 wherein the movement assembly comprises at least one biasing member coupled to the lens body.

8. The intraocular lens of claim 1 wherein the movement assembly is adapted to cooperate with at least one of the ciliary muscle of the mammalian eye, the zonules of the mammalian eye and the vitreous pressure in the eye to effect accommodating movement of the lens body in the eye.

9. The intraocular lens of claim 8 wherein the movement assembly is adapted to cooperate with the ciliary muscle, to move the lens body toward a first position relative to the retina of the eye when the ciliary muscle is relaxed and toward a different second position relative to the retina of the eye when the ciliary muscle is contracted.

10. The intraocular lens of claim 9 wherein the movement assembly comprises at least one biasing member coupled to the lens body.

11. The intraocular lens of claim 1 wherein the movement assembly comprises at least one fixation member including a proximal end region coupled to the lens body and distal end region extending away from the lens body and adapted to contact a capsular bag of the mammalian eye.

12. The intraocular lens of claim 6 wherein the movement assembly comprises at least one fixation member including a proximal end region coupled to the lens body and distal end region extending away from the lens body and adapted to contact a capsular bag of the mammalian eye.

13. The intraocular lens of claim 9 wherein the movement assembly comprises at least one fixation member including a proximal end region coupled to the lens body and distal end region extending away from the lens body and adapted to contact a capsular bag of the mammalian eye.

14. The intraocular lens of claim 1 which provides enhanced accommodation performance relative to a similar intraocular lens having a single optical power.

15. The intraocular lens of claim 1 which provides enhanced accommodation performance relative to a similar intraocular lens located in a substantially fixed position in the eye.

16. The intraocular lens of claim 1 which provides enhanced accommodation performance for viewing near objects relative to a similar intraocular lens having a single optical power, and enhanced intermediate vision and a greater range of near vision relative to a similar intraocular lens located in a substantially fixed position in the eye.

17. A combination comprising:

a lens body sized and adapted for placement in a mammalian eye, and the lens body having a central axis and a plurality of different optical powers, the lens body including a central region about the central axis and at least one annular region extending radially outwardly from the central axis, the central region and the at least one annular region each having a different optical power; and a movement assembly joined to the lens body and adapted to cooperate with the mammalian eye to effect accommodating movement of the lens body in the eye; and a lens element adapted for implantation in a capsular bag of the eye.

18. The combination of claim 17 wherein the lens element is adapted for implantation in a substantially fixed position in the capsular bag of the eye, and has a single optical power.

19. The combination of claim 17 wherein the lens element is adapted to reduce cell growth in the capsular bag of the mammalian eye.

20. The combination of claim 17 wherein both the lens body and the lens element are adapted for implantation in the capsular bag of the mammalian eye with the lens body being located anterior of the lens element.

* * * * *